United States Patent
Balestracci et al.

(10) Patent No.: US 6,193,688 B1
(45) Date of Patent: Feb. 27, 2001

(54) TAMPER EVIDENT PROTECTOR CAP FOR PRE-FILLED SYRINGE BARRELS

(75) Inventors: Ernest Balestracci, Iselin; John J. Niedospial, Jr., Burlington, both of NJ (US)

(73) Assignee: Bracco Diagnostics, Inc., Princeton, NJ (US)

( * ) Notice: Subject to any disclaimer, the term of this patent is extended or adjusted under 35 U.S.C. 154(b) by 0 days.

(21) Appl. No.: 09/617,900

(22) Filed: Jul. 17, 2000

(51) Int. Cl.[7] .................................................. A61M 5/00
(52) U.S. Cl. .................................................. 604/111
(58) Field of Search .................................. 604/111, 110, 604/187, 232

(56) References Cited

U.S. PATENT DOCUMENTS

| 4,667,837 | 5/1987 | Vitello et al. | 215/228 |
| 4,886,497 | 12/1989 | Scholl, Jr. | 604/111 |
| 5,328,474 | 7/1994 | Raines | 604/110 |
| 5,624,402 | 4/1997 | Imbert | 604/111 |

*Primary Examiner*—John D. Yasko
(74) *Attorney, Agent, or Firm*—Imre Balogh

(57) ABSTRACT

A tamper evident protector cap for a pre-filled syringe or cartridge barrel stoppered by an elastomeric closure. The protector cap securely retains the elastomeric closure during in-line processing, handling and shipment. The protector cap includes frangible brackets which on tampering break away from the protector cap evidencing that product integrity might have been jeopardized and the product should not be used.

7 Claims, 4 Drawing Sheets

TAMPER EVIDENT PROTECTOR CAP FOR PRE-FILLED SYRINGE BARRELS

BACKGROUND OF THE INVENTION

1. Field of the Invention

This invention relates to a tamper evident protector cap for a pre-filled syringe barrel. More particularly, the invention relates to a cap for a syringe barrel containing a liquid medication therein for securely holding a closure in the tapered tip of the syringe barrel and serving as a tamper evident indicator.

2. Reported Developments

Pre-filled syringe barrels or cartridges containing injectable solutions therein are stoppered by elastomeric closures, such as soft rubber stoppers at the distal, tapered end thereof, while the proximal end of the barrels are closed by slidable plungers. The pre-filled syringe barrels or cartridges are sterilized, such as by autoclaving, and packaged ready for use.

It has been observed that during in-line processing, handling, and sterilizing the pre-filled barrels some elastomeric closures were missing from the tips of the barrels resulting in rejects. Also, during shipment of the finished product and handling by healthcare professionals some untipped barrels were observed which necessitated the discarding of batches containing failed samples. For product integrity a corrective measure was indicated to prevent the elastomeric closure from becoming dislodged from the tip of the barrel.

More importantly, it has also been recognized that untipped barrels (whether the damage occurred during shipment or handling) attracts the suspicion that the product was tampered with. Such possible tampering is a concern for both the FDA and the manufacturers who are required to insure safety, efficacy and product integrity.

SUMMARY OF THE INVENTION

In accordance with the present invention a protective cap is provided for a syringe or cartridge barrel. The syringe or cartridge barrel, comprising a cylindrical chamber containing a pharmaceutical or biological liquid in the form of an injectable solution, terminates in a tapered tip having a bore therethrough. The tapered tip is equipped with a female luer connector barrel to which a male luer connector or an injection needle may be attached. The bore in the tapered tip is stoppered by an elastomeric closure, such as a soft rubber plug. The protective cap covering the tapered tip comprises a cylindrical top portion; and a bottom skirt portion having: two semi-circular walls facing each other and spaced 180° from each other; and two frangible brackets facing each other and spaced 180° from each other, each of the brackets terminating in a horizontal leg adapted to engage the female luer connector barrel. The two semi-circular walls provide strength and rigidity to the protector cap, while the brackets are designed to disengage the female luer connector barrel thereby allowing easy removal of the protector cap. At the point of disengagement the brackets break away from the skirt portion of the protector cap indicating that the protector cap has been removed from the tip of the syringe or cartridge barrel.

DETAILED DESCRIPTION OF THE INVENTION

Figure 1:
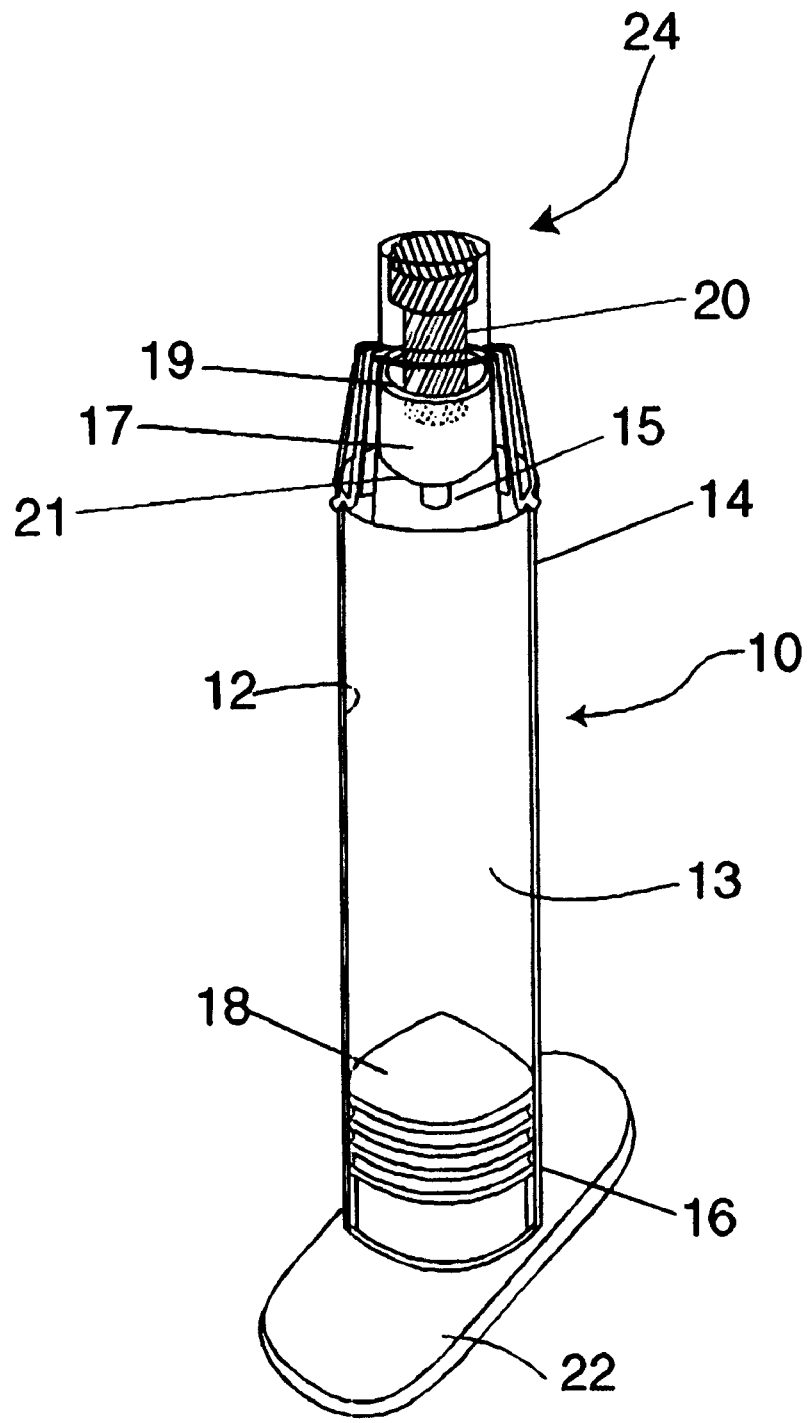
FIG. 1 is a perspective view of a syringe barrel equipped with the tamper evident protector cap of the present invention.

FIG. 1 shows a typical syringe or cartridge barrel generally designated by the numeral 10, made of glass or a polymeric material having an inner surface 12 defining a cylindrical chamber 13 for retaining a pharmaceutical or biological liquid therein. The barrel has a distal end 14 terminating in a tapered tip 15 having a bore therethrough to which an injection needle or a luer connector with a tubing conduit can be attached, and a proximal end 16 for receiving a plunger 18 which retains the pharmaceutical or biological liquid in the barrel and which, upon use, expels the pharmaceutical or biological liquid from the barrel when an external pressure is exerted on the plunger. The tapered tip 15 having a bore therein is stoppered by a resilient closure 20, such as an elastomeric closure or a soft rubber stopper, for hermetically sealing the distal end of the barrel. At its proximal end 16 the barrel is equipped with an integral flange 22 to facilitate the handling of the barrel. When the pharmaceutical or biological liquid is an injectable solution, the barrel along with its content is sterilized, preferably by autoclave. After sterilization the barrel is packaged and stored ready for use when needed. Delivery of the injectable solution is accomplished by removing the resilient closure from the tapered tip and attaching an injection needed or a luer connector onto the tapered tip of the barrel.

Surrounding the tapered tip 15, a female luer connector barrel 17 is provided for attachment of a male luer connector or an injection needle thereto. The luer connector barrel comprises an open distal end 19, and a closed proximal end 21.

To prevent the risk of fall out of the resilient closure from the tip of the barrel and to insure product integrity against tampering, a protector cap, generally designated by the numeral 24, covers the tip 15 of barrel 10 and securely holds resilient closure 20 in the barrel.

Figure 2:
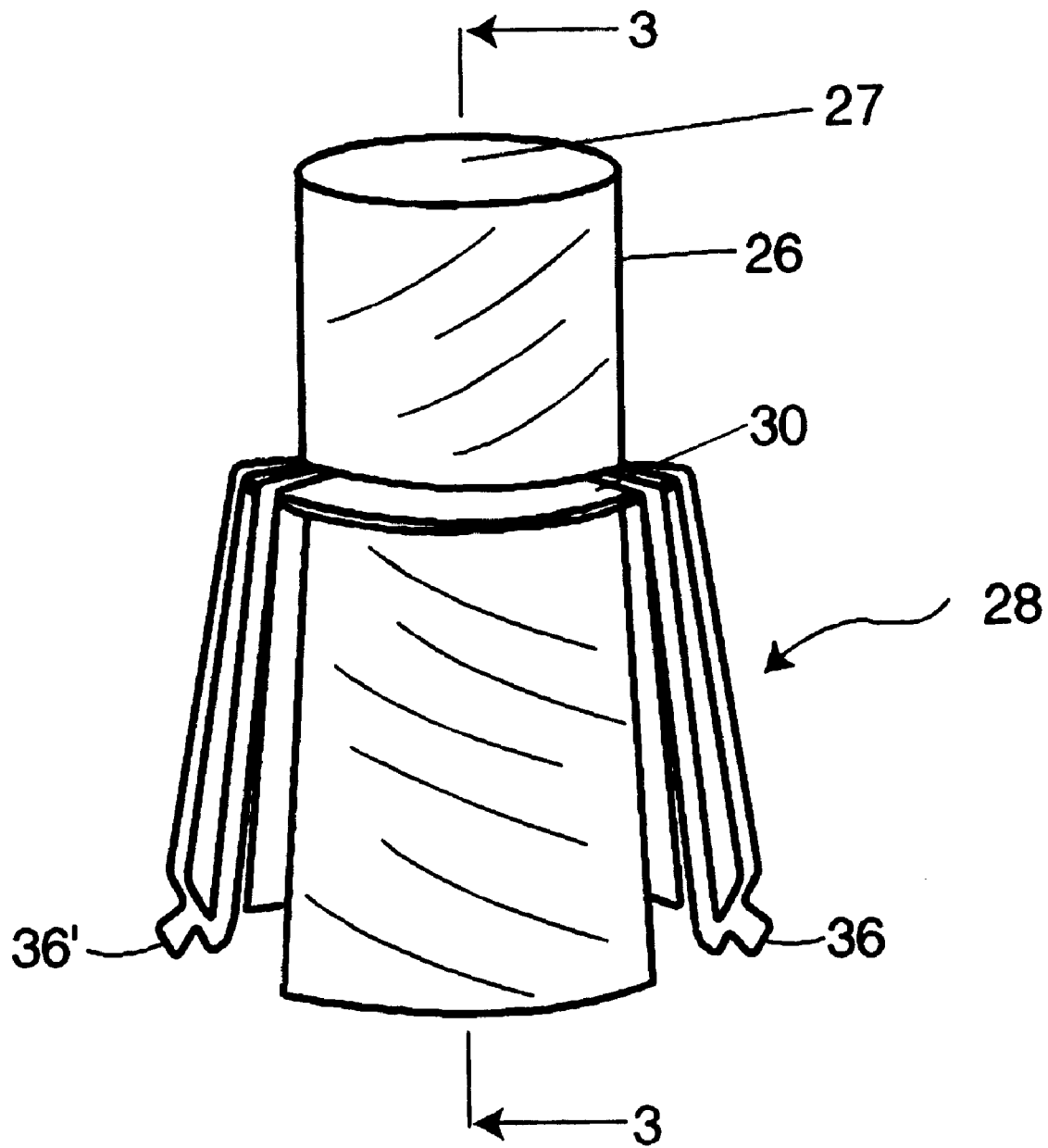
FIG. 2 is a perspective view of the tamper evident protector cap removed from the syringe barrel.
Figure 3:
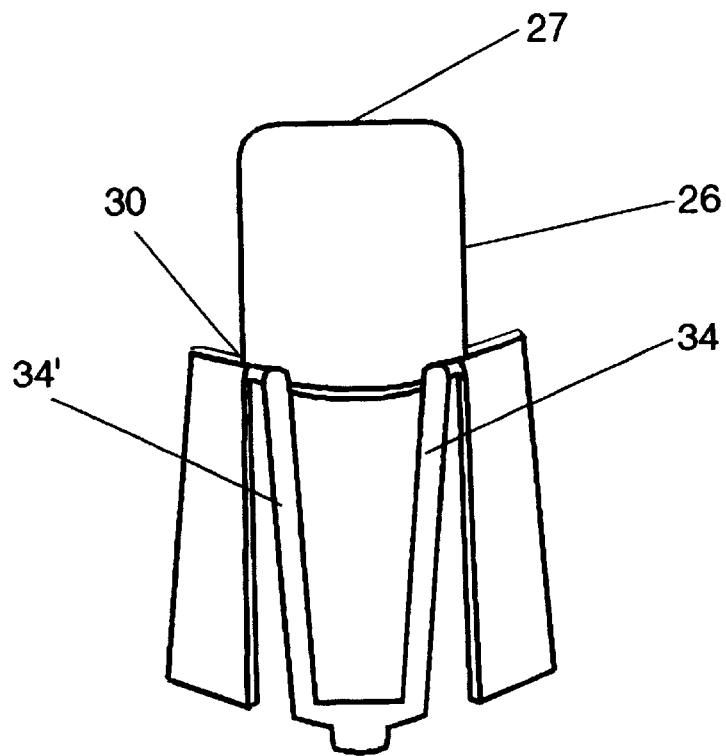
FIG. 3 is a side elevational view of the tamper evident protector cap taken along the line 3—3 of FIG. 2.
Figure 4:
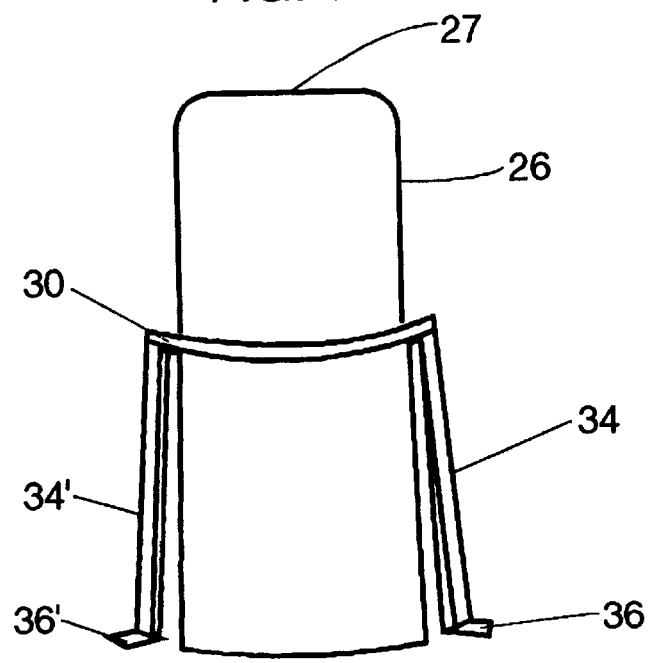
FIG. 4 is another side elevational view of the tamper evident protector cap turned 90° from that shown in FIG. 3.
Figure 5:
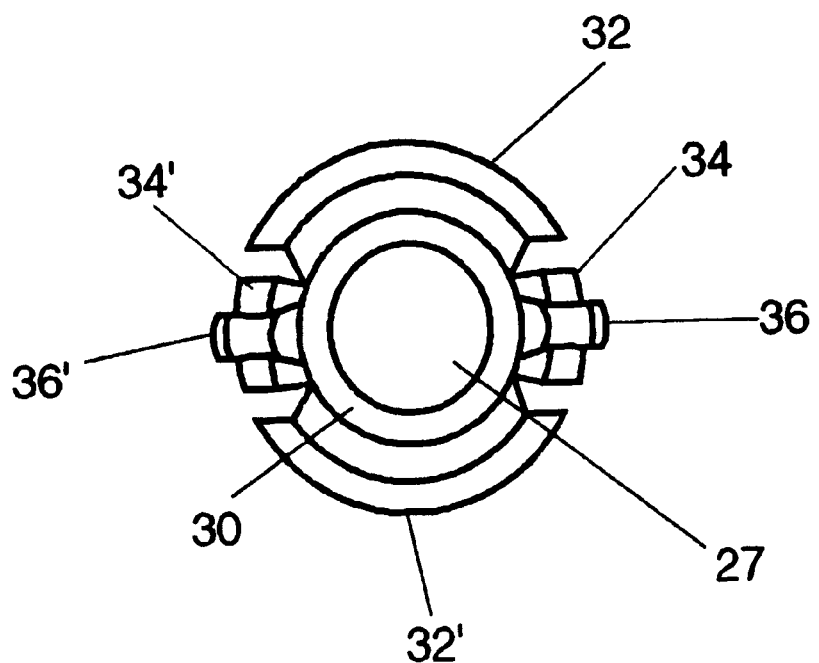
FIG. 5 is a bottom plan view of the tamper evident protector cap.
Figure 6:
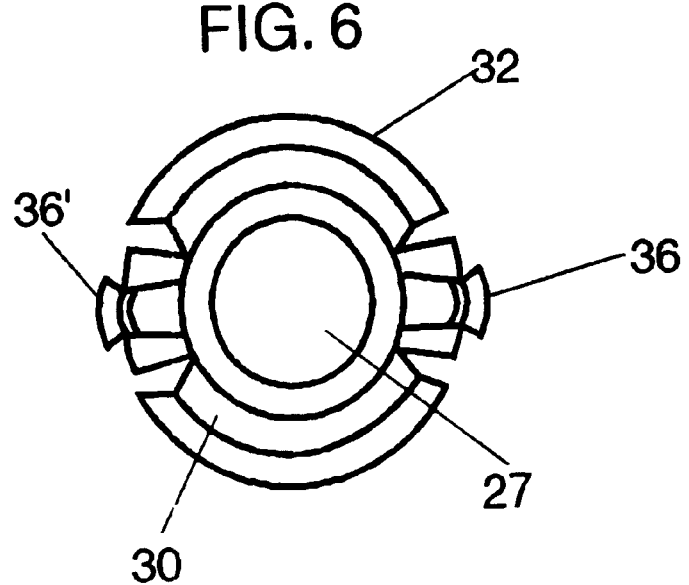
FIG. 6 is a top plan view thereof.

Reference is now made to FIGS. 2–6 wherein: FIG. 2 is a perspective view of the protector cap; FIG. 3 is a side elevational view of the protector cap; FIG. 4 is another side elevational view of the protector cap turned 90° from that shown in FIG. 3; and FIG. 5 and FIG. 6 are bottom plan and top plan view, respectively, of the protector cap. Protector cap 24 comprises: a cylindrical top portion 26 terminating in a circular surface 27, and a bottom somewhat larger cylindrical skirt portion, generally designated by the numeral 28. Skirt portion comprises: a distal top portion 30 extending into top cylindrical portion 26; two semi-circular walls 32 and 32' facing each other and spaced 180° from each other; two frangible brackets 34 and 34' facing each other and spaced 180° from each other, each of the frangible brackets terminating in a horizontal leg 36 and 36'.

The protector cap 24 is made of a polymeric material including: polyolefins such as polyethylene and polypropylene; polystyrene, polycarbonate, polymethylpentene, cyclic olefin copolymers, acrylic polymers and methacrylic polymers.

As shown in FIG. 1, protector cap 24 encloses the resilient closure 20 and locks over the luer connector barrel 17. The two frangible brackets 34 and 34' having horizontal legs 36 and 36' engage the proximal end 21 of the luer connector barrel 17 when the protector cap 24 is placed on the tapered tip 15 of the syringe or cartridge barrel 10. The positioning of the protector cap onto the tip of the barrel is accomplished by snapping the protector cap downward so that the horizontal legs 36 and 36' lock over the luer connector barrel 17. Once the protector cap is snapped on the luer connector barrel, it will securely hold the resilient closure in place.

FIGS. 3 and 4 show side elevational views of the protector cap subsequent to its removal from the tip of the barrel. Upon removal of the protector cap by a twisting or lifting motion the frangible brackets 34 and 34' crack and horizontal legs 36 and 36' are released from holding onto the proximal end of the luer connector barrel 21. If the protector cap is tampered with, the healthcare professional will readily observe the separated brackets not holding onto the tapered tip of the syringe or cartridge barrel. The product then will not be used and will be returned to the manufacturer with complaints.

The tamper evident protector cap may also be secured to the tip of the syringe barrel by a bonding adhesive or a solvent. It is also contemplated that the resilient closure or plug may be manufactured integral with the tamper evident protector cap wherein the resilient closure is to be made of a thermoplastic elastomer allowing the use of a two shot mold manufacturing.

PARTS LIST

| | |
|---|---|
| Syringe or cartridge barrel | 10 |
| Inner surface of syringe or cartridge barrel | 12 |
| Cylindrical chamber defined by the inner surface | 13 |
| Distal end of barrel | 14 |
| Tapered tip of barrel | 15 |
| Proximal end of barrel | 16 |
| Luer connector barrel | 17 |
| Plunger | 18 |
| Open distal end of luer connector barrel | 19 |
| Resilient closure | 20 |
| Closed proximal end of luer connector barrel | 21 |
| Flange of the barrel | 22 |
| Protector cap, generally designated | 24 |
| Top cylindrical portion of protector cap | 26 |
| Flat circular surface of protector cap | 27 |
| Bottom cylindrical skirt portion of protector cap, generally designated | 28 |
| Distal top portion of the skirt portion | 30 |
| Two semi-circular walls of skirt portion | 32 & 32' |
| Two frangible brackets | 34 & 34' |
| Two horizontal legs on the frangible brackets | 36 & 36' |

Various modifications of the present invention disclosed will become apparent. This invention is intended to include such modifications to be limited only by the scope of the claims.

What is claimed is:

1. A tamper evident protector cap for a pre-filled glass or plastic syringe or cartridge barrel stoppered by an elastomeric closure at its tapered distal end comprising:
    a cylindrical top portion; and
    a bottom skirt portion having: two semicircular walls facing each other and being spaced 180° from each other; two frangible brackets facing each other and being spaced 180° from each other, having a top portion and a bottom portion; and
    a horizontal leg on the bottom portion of each of said brackets, wherein
        said top portions of said brackets are frangible and said horizontal leg on the bottom portion of each of said bracket is adapted to engage the tapered distal end of a pre-filled syringe or cartridge barrel.

2. The tamper evident protector cap of claim 1 made of a polymeric material selected from the group consisting of polyethylene, polypropylene, polystyrene, polycarbonate, polymethylpentene, cyclic olefin copolymers, acrylic polymers and methacrylic polymers.

3. A tamper evident protector cap and a syringe or cartridge barrel combination wherein said syringe or cartridge barrel comprises:
    a) a cylindrical chamber having a tapered distal end terminating in a tip having a bore therethrough, said bore is stoppered by an elastomeric closure, said cylindrical chamber containing an injectable solution therein, wherein said tip is equipped with a female luer connector barrel to which a male luer connector or an injection needle may be attached, said female luer connector barrel comprises an open distal end and a closed proximal end;
        an open proximal end for receiving a slidable elastomeric plunger for retaining an expelling the injectable solution from the cylindrical chamber;
    b) wherein said tamper evident protector cap is removably being engaged with said syringe or cartridge barrel and comprises:
        a cylindrical top portion terminating in a flat circular surface conforming to and retaining said elastomeric closure in said bore;
        a skirt portion comprising: a distal top portion extending into said cylindrical top portion and being integral therewith; two semicircular walls facing each other and being spaced 180° from each other covering said female luer connector barrel; two frangible brackets facing each other and being spaced 180° from each other each of which terminates in a horizontal leg, said horizontal legs engaging the closed proximal end of said female luer connector barrel, wherein upon disengagement of said tamper evident protector cap from said female luer connector barrel, said brackets break away from the skirt portion of the protector cap thereby indicating that the tamper evident protector cap has been removed.

4. The tamper evident protector cap and the syringe or cartridge barrel combination of claim 3 wherein the tamper evident protector cap is made of a polymeric material selected from the group consisting of polyethylene, polypropylene, polystyrene, polycarbonate, polymethylpentene, cyclic olefin copolymers, acrylic polymers and methacrylic polymers.

5. The tamper evident protector cap and the syringe or cartridge barrel combination of claim 3 wherein said elastomeric closure is a soft rubber stopper.

6. The tamper evident protector cap and the syringe or cartridge barrel combination of claim 3 wherein said injectable solution is a pharmaceutical or biological liquid.

7. The tamper evident protector cap and the syringe or cartridge barrel combination of claim 3 wherein said combination containing the injectable solution therein is sterilized by autoclave.

* * * * *